United States Patent [19]

Cohen

[11] 4,192,816

[45] Mar. 11, 1980

[54] MIXTURES OF 3-PENTENENITRILES AND 3-METHYLENE-PENTANENITRILES

[75] Inventor: Noal Cohen, Montclair, N.J.

[73] Assignee: Hoffmann-La Roche Inc., Nutley, N.J.

[21] Appl. No.: 970,037

[22] Filed: Dec. 15, 1978

Related U.S. Application Data

[62] Division of Ser. No. 873,184, Jan. 30, 1978, abandoned.

[51] Int. Cl.$^2$ .................. C07C 121/70; C07D 311/72
[52] U.S. Cl. ............................. 260/465 D; 260/345.5
[58] Field of Search ............ 260/465 D, 465 F, 345.5

[56] References Cited

U.S. PATENT DOCUMENTS 3,947,473  3/1976  Scott et al. .................. 260/465 D X

OTHER PUBLICATIONS

Gokel et al., Tetrahedron Letters No. 39, pp. 3495–3496 (1976).

Mayer et al., Helv. Chim. Acta., 46, p. 650 (1963).

*Primary Examiner*—Dolph H. Torrence
*Attorney, Agent, or Firm*—Jon S. Saxe; Bernard S. Leon; William H. Epstein

[57] ABSTRACT

Preparation of chroman-2-acetic acid from 2-hydroxy-chromanes or derivatives thereof and intermediates in this synthesis.

2 Claims, No Drawings

MIXTURES OF 3-PENTENENITRILES AND 3-METHYLENE-PENTANENITRILES

This is a division of application Ser. No. 873,184 filed Jan. 30, 1978, and now abandoned.

SUMMARY OF INVENTION

In accordance with this invention, a new and improved synthesis is provided for converting a compound of the formula:

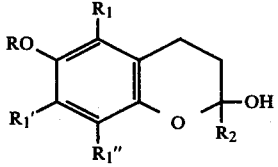

wherein R is hydrogen or taken together with its attached oxygen atoms forms an ester protecting group removable by hydrolysis; R', $R_1'$ and $R_1''$ are independently hydrogen or lower alkyl and $R_2$ is lower alkyl to a compound of the formula

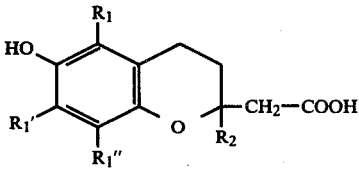

wherein R, $R_1$, $R_1'$, $R_1''$ and $R_2$ are as above.

The compounds of formula II are known as antioxidants and the compound where $R_1$, $R_1'$, $R_1''$ and $R_2$ are methyl is an intermediate in the production of Vitamin E. See U.S. Pat. No. 4,026,907 issued May 31, 1977, Scott et al.

DETAILED DESCRIPTION

As used throughout this application, the term "lower alkyl" comprehends both straight and branched chain saturated hydrocarbon groups containing from 1 to 7 carbon atoms, such as methyl, ethyl, propyl, isopropyl, etc. As used throughout this application, the term "halogen" includes all four halogens, such as bromine, chlorine, fluorine and iodine. The term "alkali metal" includes sodium, potassium and lithium.

Also as used herein, the term "aryl" signifies mononuclear aromatic hydrocarbon groups, such as phenyl, which can be unsubstituted or substituted in one or more positions with a lower alkyl substituent as well as polynuclear groups such as naphthyl, anthryl, phenanthryl, azulyl, etc., which can be substituted with one or more of the aforementioned groups. Preferred aryl groups are substituted and unsubstituted mononuclear aryl groups particularly phenyl and tolyl. The term "aryl lower alkyl" comprehends groups where the aryl and lower alkyl are defined as above, particularly benzyl. The term "aroic acid" comprehends acids wherein the aryl group is defined as above. The preferred aroic acid is benzoic acid.

Still further used herein, the term "ester protecting group removable by hydrolysis" comprehends any conventional organic acid protecting group which can be removed by hydrolysis. The preferred organic acid protecting groups are the lower alkanoic acids containing from 2 to 7 carbon atoms such as acetic acid, proprionic acid, etc., as well as the aroic acids such as benzoic acid.

In accordance with this invention, the compound of formula I where R is other than hydrogen, i.e. a compound of the formula

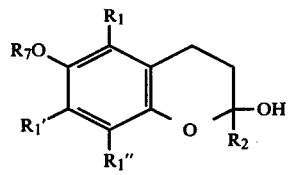

wherein $R_1$, $R_1'$, $R_1''$ and $R_2$ are as above; and $R_7$ taken together with the attached oxygen atom forms an ester protecting group removable by hydrolysis is converted to the compound of formula II via the following intermediates:

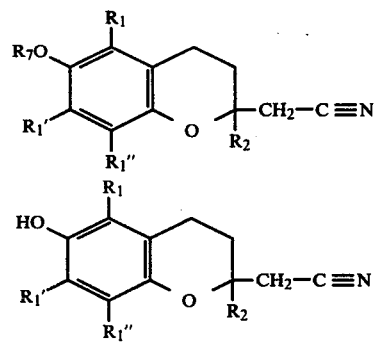

wherein $R_1$, $R_1'$, $R_1''$, $R_2$ and $R_2$ are as above.

In converting the compound of formula I-A to a compound of formula III, the compound of formula I-A is reacted with a compound of the formula

$$N \equiv C-CH_2-COOH \qquad VI$$

in the presence of a compound of the formula

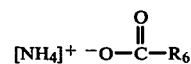

wherein $R_6$ is lower alkyl or aryl.

The reaction of the compound of formula I-A with a compound of formula VI to produce a compound of the formula III is carried out in the presence of an organic solvent. Among the preferred solvents are the aromatic hydrocarbon solvents such as toluene, benzene, xylene, etc. Any conventional inert organic solvent having a boiling point of greater than 80° C. can be utilized in carrying out this reaction. Generally, this reaction is carried out utilizing conventional Knoevenagel condensation conditions such as disclosed in G. Jones, *Organic Reactions*, 15, 204 (1967). Generally, this reaction is carried out in the presence of an organic amine base such as pyridine. However, tri(lower alkyl)amine bases such as tri(ethyl)amine, tri(methyl)amine, etc. can be utilized. In carrying out this reaction, temperatures of from 80° C. to 150° C. are utilized.

The compound of formula III can be directly converted to the compound of formula II by treating the compound of formula III with a strong, inorganic base such as an alkali metal hydroxide, i.e., potassium hydroxide, sodium hydroxide, etc. In carrying out this reaction, temperatures of from 100° C. to 200° C. are generally utilized. Generally, this reaction is carried out in a high boiling, organic solvent such as ethylene glycol as well as other inert organic solvents mentioned hereinbefore.

On the other hand, the compound of formula III can be converted to the compound of formula II via the intermediate of formula IV. In this method, the compound of formula III is treated with an alkali metal carbonate or alkali metal bicarbonate at a temperature of from 20° C. to 65° C. In carrying out this reaction, any conventional inert organic solvent as well as water can be utilized. Generally, this reaction is carried out at temperatures of from 20° C. to 65° C. The compound of formula IV can be converted to the compound of formula II by treatment with a strong base such as an alkali metal hydroxide under the conditions set forth for the conversion of a compound of formula III directly to a compound of formula II.

In accordance with another embodiment of this invention, the compound of formula I can be converted to the compound of formula II via the following intermediates:

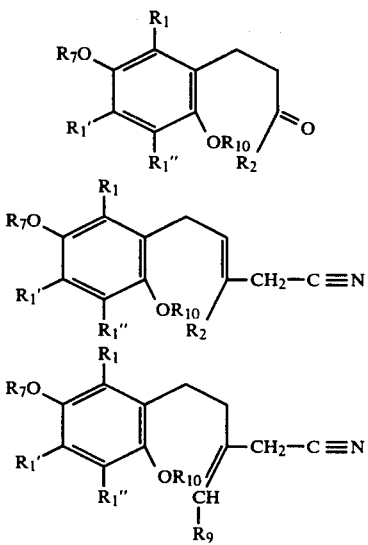

wherein $R_1$, $R_1'$, $R_1''$, $R_2$ and $R_7$ are as above, $R_{10}$ is lower alkanoyl or benzoyl and $R_9$ is hydrogen or lower alkyl containing from 1 to 6 carbon atoms.

The compound of formula I is converted to the compound of formula X by treating the compound of formula I-A with an esterifying agent such as a lower alkanoic acid or benzoic acid or a reactive derivative thereof. Any conventional method of esterifying a hydroxy group can be utilized in carrying out this reaction. Among the preferred methods is by treating the compound of formula I with a lower alkanoic acid anhydride such as acetic acid anhydride in the presence of a base such as pyridine.

The compound of formula X is treated via a standard Knoevenagel reaction with cyanoacetic acid in the presence of a compound of the formula VII. Generally this reaction is carried out in the presence of an inert organic solvent at reflux. In carrying out this reaction, a conventional inert organic solvent, preferably the high boiling aromatic hydrocarbon solvent such as mentioned hereinbefore can be utilized. If desired, the reaction can be carried out in the presence of a lower alkanoic acid such as acetic acid in a mixed with a high boiling aromatic hydrocarbon solvent. This reaction produces a mixture containing the compound of formula XI-A and XI-B. This mixture need not be separated since it can be directly converted to the compound of formula II.

The mixture of the compounds of formula XI-A and XI-B is converted to the compound of formula IV by treating this mixture with an alkali metal lower alkoxide. In carrying out this reaction, temperatures of from 0° C. to 30° C. can be utilized. Furthermore, this reaction is carried out in the presence of a lower alkanol solvent. Any conventional lower alkanol such as methanol, ethanol, isopropanol, n-butanol can be utilized.

On the other hand, it has been discovered that the mixture compounds of formula XI-A and XI-B can be directly converted to a compound of formula II by treating this mixture with a strong base at a temperature of from 100° C. to 200° C. In carrying out this reaction the same conditions described in connection with the conversion of the compound of formula III to a compound of formula II can be utilized.

In accordance with another embodiment of this invention, the compound of formula I can be directly converted in high yields to the compound of formula IV by reacting the compound of formula I with acetonitrile in the presence of a strong base. In carrying out this reaction, any strong base can be utilized. Among the preferred strong bases are included the alkali metal hydroxides such as sodium or potassium hydroxide. This base also cleaves R where R forms an ester protecting group. The acetonitrile can be utilized as the reaction medium. Therefore, it is preferable to carry out this reaction in excess acetonitrile. On the other hand, this reaction is generally carried out at the reflux temperature of the reaction medium.

The following examples are illustrative but not limitative of the present inventions. The ether utilized was diethyl ether. All temperatures are in degrees centigrade.

In the examples, all reactions were carried out under an atmosphere of argon. The "usual work-up" involves 3 extractions with the specified solvent. The organic extracts were washed with water and saturated brine then dried (MgSO$_4$), filtered and concentrated at 40–50° on a rotary evaporator. The residue was further dried under high vacuum. Column chromatography was performed using silica gel, 0.063–0.2 mm. In the examples, the ether used was diethyl ether.

EXAMPLE 1 rac.-6-Acetyloxy-3,4-dihydro-2,5,7,8-tetramethyl-2H-1-benzopyran-2-acetonitrile

A solution of 26.4 g (0.1 mole) of rac.-2-hydroxy-6-acetoxy-3,4-dihydro-2,5,7,8-tetramethyl-2H-1-benzopyran, 8.5 g (0.1 mol) of cyanoacetic acid and 300 mg of ammonium acetate in 11 ml of pyridine and 20 ml of toluene was stirred and refluxed for 18 hr with water removal. The reaction mixture was cooled to room temperature and filtered. The filtrate was diluted with ether and washed twice with 3 N aqueous HCl and once each with saturated aqueous NaHCO$_3$ and brine. The organic solution was processed in the usual manner to give 24.1 g of a yellow solid. This material was dissolved in 110 ml of hot ether and cooled to 0°. The precipitated material was filtered off. The filtrate was concentrated on a rotary evaporator and then chromatographed on 250 g of silica gel. Elution with 2:1 parts by volume and 1:1 parts by volume hexane-ether afforded 8.44 g (29%) of rac.-6-acetyloxy-3,4-dihydro-2,5,7,8-tetramethyl-2H-1-benzopyran-2-acetonitrile as a white solid. A sample of this material was recrystallized from ethyl acetate to give white crystals, m.p. 122–123° C.

EXAMPLE 2

Rac.-3,4-Dihydro-6-hydroxy-2,5,7,8-tetramethyl-2H-1-benzopyran-2-acetonitrile

A mixture of 581 mg (2.02 mmoles) of rac.-6-acetyloxy-3,4-dihydro-2,5,7,8-tetramethyl-2H-1-benzopyran-2-acetonitrile and 418 mg (3.03 mmoles) of $K_2CO_3$ in 17 ml of methanol and 3 ml of water was stirred at room temperature for 64 hr. The resulting mixture was poured into water and worked-up with ether in the usual manner giving 480 mg of a tan solid. This material was triturated with cold ether to give 340 mg (69%) of a tan solid. A sample of this material was recrystallized from toluene yielding pure rac. 3,4-dihydro-6-hydroxy-2,5,7,8-tetramethyl-2H-1-benzopyran-2-acetonitrile as a tan solid mp 162–163°.

EXAMPLE 3 rac.-(6-Hydroxy-3,4-dihydro-2,5,7,8-tetramethyl-2H-1-benzopyran-2-yl)acetic Acid A mixture of 1.0 g (3.48 mmoles) of rac.-6-acetyloxy-3,4-dihydro-2,5,7,8-tetramethyl-2H-1-benzopyran-2-acetonitrile, 1.0 g (15.2 mmoles) of 85% KOH, 1 ml of water and 8 ml of ethylene glycol was stirred and refluxed for 16 hr. The reaction mixture was cooled to room temperature, then poured into water. The pH of the solution was adjusted to 8 with 1 N aqueous HCl. The resulting mixture was extracted with two portions of ether (the ether extracts were discarded). The aqueous phase was acidified with 3 N aqueous HCl and worked-up with ether in the usual manner giving 756 mg (82%) of rac.-(6-hydroxy-3,4-dihydro-2,5,7,8-tetramethyl-2H-1-benzopyran-2-yl)acetic acid as a tan solid.

EXAMPLE 4

Mixture of E-and Z-3-Methyl-5-(2,4,5-trimethyl-3,6-diacetyloxyphenyl)-3-pentenenitrile and 3-Methylene-5-(2,4,5-trimethyl-3,6-diacetyloxyphenyl)pentanenitrile A solution of 1.62 g (5.29 mmoles) of 4-(2,5-diacetoxy-3,4,6-trimethylphenyl)butane-2-one, 487 mg (5.73 mmoles) of cyanoacetic acid, 200 mg of ammonium acetate and 0.5 ml of acetic acid in 5 ml of toluene was stirred and refluxed with water removal. A dense precipitate formed rapidly and 8 ml of additional toluene were added. Refluxing was continued for 23 hr then the reaction mixture was cooled to room temperature and filtered. The filtrate was diluted with ether, washed twice with saturated aqueous $NaHCO_3$ solution and worked-up in the usual manner to give 1.34 g (77%) of a mixture of E-and Z-3-methyl-5-(2,4,5-trimethyl-3,6-diacetyloxyphenyl)-3-pentenenitrile and 3-methylene-5-(2,4,5-trimethyl-3,6-diacetyloxy-phenyl)pentanenitrile as a yellow solid.

EXAMPLE 5 rac. 3,4-dihydro-6-hydroxy-2,5,7,8-tetramethyl-2H-1-benzopyran-2-acetonitrile

A slurry of 500 mg (1.52 mmoles) of the mixture of E-and Z-3-methyl-5-(2,4,5-trimethyl-3,6-diacetyloxyphenyl)-3-pentenenitrile and 3-methylene-5-(2,4,5-trimethyl-3,6-diacetyloxy-phenyl)pentanenitrile in 5 ml of methanol was treated with 0.71 ml (3.34 mmoles) of a 4.7 M methanolic sodium methoxide solution. The resulting mixture was stirred at room temperature for 4.5 hr, then poured into 20 ml of water and worked-up with ether in the usual manner affording 345 mg (93%) of rac. 3,4-dihydro-6-hydroxy-2,5,7,8-tetramethyl-2H-1-benzopyran-2-acetonitrile as a tan solid.

EXAMPLE 6 rac.-(6-Hydroxy-3,4-dihydro-2,5,7,8-tetramethyl-2H-1-benzopyran-2-yl)acetic acid A mixture of 623 mg (1.89 mmoles) of the mixture of E-and Z-3-methyl-5-(2,4,5-trimethyl-3,6-diacetyloxyphenyl)-3-pentenenitrile and 3-methylene-5-(2,4,5-trimethyl-3,6-diacetyloxy-phenyl)pentanenitrile, 498 mg (7.70 mmoles) of 85% KOH, 5 ml of ethylene glycol and 0.5 ml of water was stirred and refluxed for 36 hr. The reaction mixture was cooled to room temperature, then poured into water. The pH of the solution was adjusted to 8 with 1 N aqueous HCl and the resulting mixture was extracted with two portions of ether (the extracts were discarded). The aqueous phase was acidified with 3 N aqueous HCl and worked-up with ether in the usual manner giving 421 mg (84%) of rac.-(6-hydroxy-3,4-dihydro-2,5,7,8-tetramethyl-2H-1-benzopyran-2-yl)acetic acid as a tan solid, mp 168°–170°.

EXAMPLE 7

A mixture of 9.0 g (40.5 mmoles) of 2,6-dihydroxy-2,5,7,8-tetramethylchroman and 4.54 g (69 mmoles) of 85% KOH in 61 ml of acetonitrile was rapidly stirred and refluxed for 4 hr. The dark-colored mixture, which consisted of two phases, was cooled in an ice bath and treated dropwise, with stirring, with 25 ml of 3 N aqueous HCl whereupon the reaction mixture became lighter in color. This mixture was poured into 1 N aqueous HCl and worked-up with ethyl acetate in the usual manner (the organic extracts were additionally washed with saturated aqueous $NaHCO_3$ solution) affording 14.8 g of rac.-3,4-dihydro-6-hydroxy-2,5,7,8-tetramethyl-2H-1-benzopyran-2-acetonitrile as a red solid.

EXAMPLE 8

A mixture of the rac.-3,4-dihydro-6-hydroxy-2,5,7,8-tetramethyl-2H-1-benzopyran-2-acetonitrile from Example 7 (14.8 g), 10.2 g (155 mmoles) of 85% KOH, 9 ml of water and 83 ml of ethylene glycol was stirred and refluxed for 17.5 hr. The resulting solution was cooled to room temperature and diluted with 250 ml of water. The pH of the solution was adjusted to 8 with 3 N aqueous HCl and the resulting mixture was extracted with three portions of ether (the ether extracts were discarded). The aqueous phase was further diluted with water and acidified by the dropwise addition of 3 N aqueous HCl. The resulting precipitate was filtered off and washed with water, then dried under high vacuum at room temperature for 24 hr to give 8.05 g (75%) of rac.-(6-hydroxy-3,4-dihydro-2,5,7,8-tetramethyl-2H-1-benzopyran-2-yl)acetic acid as a tan solid m.p. 169°–172° C.,

I claim:

1. A mixture of a compound of the formula

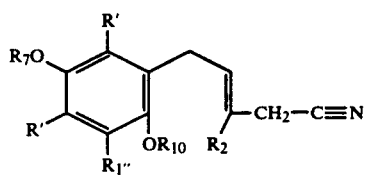

and a compound of the formula:

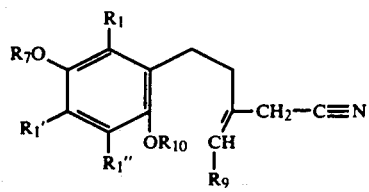

wherein $R_1$, $R_1'$ and $R''$ are hydrogen or lower alkyl; $R_7$ is lower alkanoyl, benzoyl or toluoyl; $R_2$ is lower alkyl; $R_9$ is hydrogen or lower alkyl containing from 1 to 6 carbon atoms, and $R_{10}$ is lower alkanoyl or benzoyl.

2. The compound of claim 1 wherein said compound is a mixture of E-and Z-3-methyl-5-(2,4,5,-trimethyl-3,6-diacetyloxyphenyl)-3-pentenenitrile and 3-methylene-5-(2,4,5-trimethyl-3,6-diacetyloxyphenyl)pentanenitrile.

* * * * *